United States Patent [19]

Farr

[11] Patent Number: 5,019,089
[45] Date of Patent: May 28, 1991

[54] ATHERECTOMY ADVANCING PROBE AND METHOD OF USE

[75] Inventor: Andrew F. Farr, Spring Valley, Calif.
[73] Assignee: Interventional Technologies Inc., San Diego, Calif.
[21] Appl. No.: 447,368
[22] Filed: Dec. 7, 1989
[51] Int. Cl.[5] .................................. A61B 17/32
[52] U.S. Cl. .......................... 606/172; 606/159; 606/170
[58] Field of Search .............. 606/159, 167–169, 606/170–173

[56] References Cited

U.S. PATENT DOCUMENTS

| | | | |
|---|---|---|---|
| 3,467,101 | 9/1969 | Fogarty et al. | 128/348 |
| 3,605,725 | 9/1971 | Bentov | 128/2.05 R |
| 3,731,671 | 5/1973 | Mageoh | 128/2.05 R |
| 3,913,568 | 10/1975 | Carpenter | 128/11 |
| 4,307,722 | 12/1981 | Evans | 128/344 |
| 4,320,762 | 3/1982 | Bentov | 128/343 |
| 4,444,188 | 4/1984 | Bazell et al. | 128/348 |
| 4,456,017 | 6/1984 | Miles | 128/772 |
| 4,582,181 | 4/1986 | Samson | 128/348 |
| 4,589,412 | 5/1986 | Kensey | 128/305 |
| 4,627,436 | 12/1986 | Leckrone | 128/303.1 |
| 4,646,736 | 3/1987 | Auth | 606/170 X |
| 4,650,467 | 3/1987 | Bonello et al. | 604/95 |
| 4,669,469 | 6/1987 | Gifford, III et al. | 128/305 |
| 4,679,557 | 7/1987 | Opie et al. | 128/305 |
| 4,696,667 | 9/1987 | Masch | 604/22 |
| 4,723,545 | 2/1988 | Nixon et al. | 606/171 |
| 4,732,154 | 3/1988 | Shiber | 128/305 |
| 4,921,484 | 5/1990 | Hillstead | 606/159 X |

FOREIGN PATENT DOCUMENTS 3543173 6/1986 Fed. Rep. of Germany ...... 606/167

Primary Examiner—Richard J. Apley
Assistant Examiner—J. L. Doyle
Attorney, Agent, or Firm—Nydegger & Associates

[57] ABSTRACT

An atherectomy probe for incrementally advancing a torque tube with a rotating cutter through an artery to remove obstructive tissue from the lumen of the artery comprises a fixed distal support and a moveable proximal support for slideably restraining the torque tube. The torque tube is rotated about a longitudinal axis by a motor which is slideably mounted inside a housing of a drive unit. A rod extending substantially parallel to the torque tube interconnects the distal support and the motor. The rod selectively secures the torque tube from longitudinally sliding with respect to the distal support. Adjacent to the rod is an elongated advancement tape having juxtaposed dual layers attached between the distal support and the proximal support. In its operation, a tape divider operatively engages with the advancement tape for aligning the tape. A tape advancer which cooperates with the tape divider has two pins which insert between the layers of the advancement tape for laterally extending the layers to advance the proximal support toward the distal support. An advancement lever connected to the motor is incrementally advanced in a distal direction in relation to the distal support to advance the rotating torque tube with cutter for cutting the obstructive tissue.

21 Claims, 6 Drawing Sheets

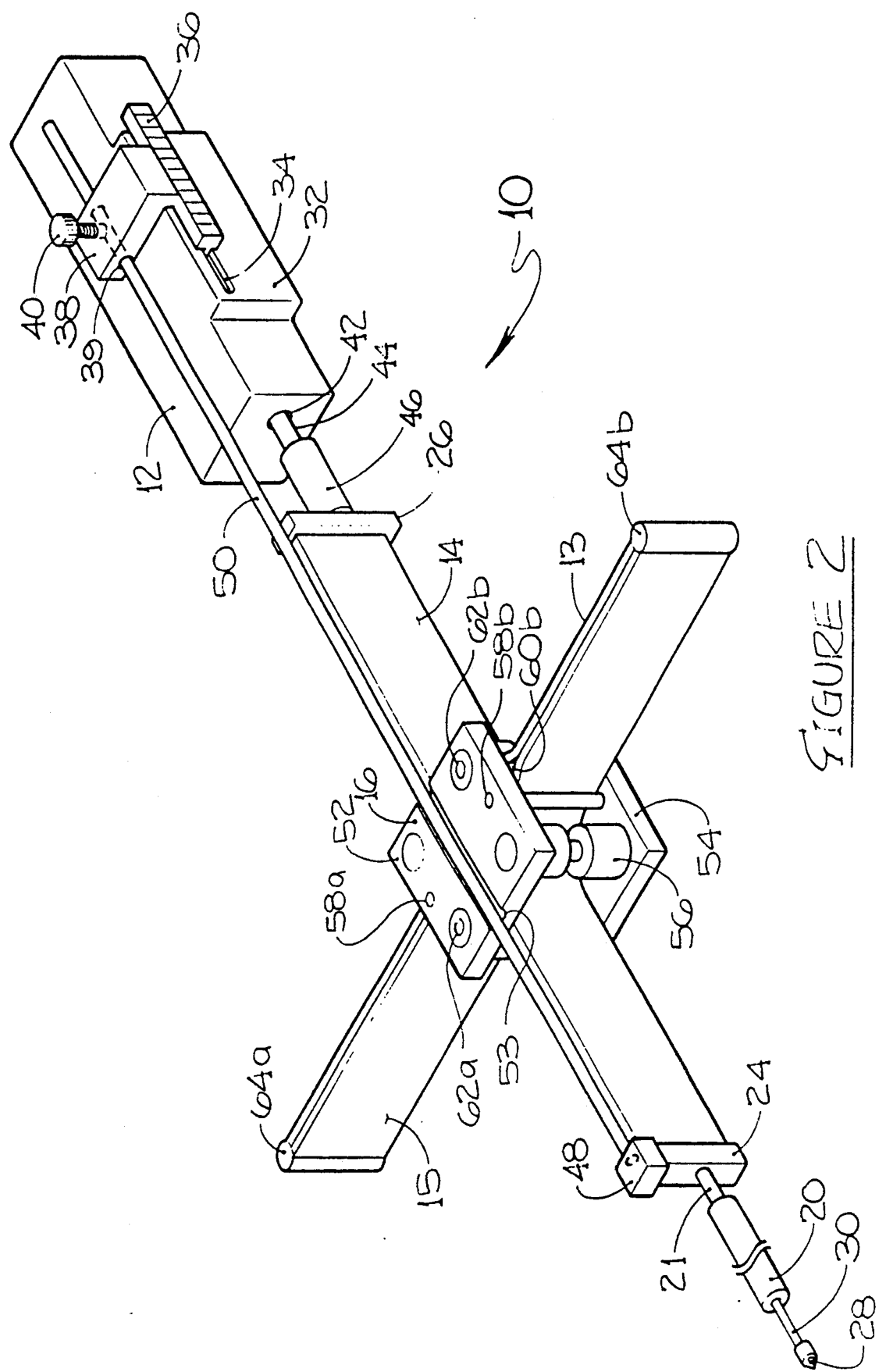

ATHERECTOMY ADVANCING PROBE AND METHOD OF USE

FIELD OF THE INVENTION

This invention relates generally to devices for controlling the removal of obstructive tissue from the lumen of arteries in humans. More particularly, the present invention pertains to an atherectomy advancing probe which is used to incrementally advance a rotating cutter and permit the cutter to extend a predetermined distance from a support sheath for drilling a passageway through obstructive tissue in the arteries. This invention is particularly, but not exclusively, useful for incrementally drilling a passageway through plaque which obstructs the flow of blood through arteries.

DISCUSSION OF THE PRIOR ART

As is well known in the medical field, blockages in coronary arteries due to the accumulation of plaque on the arterial wall will cause partial or complete stoppage of the flow of blood through these arteries. Such a condition can cause heart attacks. Similarly, when peripheral arteries are blocked with such obstructive tissue, other serious problems can result. For example, obstructive tissue in the arteries of the legs may lead to amputation of feet or limbs. Also, strokes can be caused by the build up of plaque in arteries of the head and neck, and hypertension has been linked to obstructive tissue in the renal arteries. Unquestionably, there is a need either to avoid the build up of plaque in the arteries or to provide a way to increase the flow of blood through arteries in which plaque build up has already occurred.

One method which has been used to increase the flow of blood through blocked arteries is the well known angioplasty procedure. During an angioplasty procedure, a catheter is used to place a deflated balloon in apposition to the obstructive tissue within a blocked artery. The balloon is then inflated to cause the arterial wall to expand. This expansion tears and compresses the plaque to reopen the vessel lumen for increased blood flow. One such device used in the angioplasty procedure is disclosed by T. J. Fogarty et al. in U.S. Pat. No. 3,467,101 entitled "Balloon Catheter." Unfortunately, during an angioplasty procedure, the integrity of the arterial wall may be compromised and damaged when it is stretched by inflating the balloon. Consequently, the risk is increased that future physiological problems can occur because of the damaged arterial wall. Moreover, the angioplasty procedure cannot remove plaque from the artery. Thus, since the obstructive tissue continues to remain in the artery, a recurrence of the blockage (restenosis) has been a frequent problem.

To overcome many of the problems associated with the angioplasty procedure, atherectomy procedures have been developed which cut passageways through the obstructive tissue in a blocked artery. Some atherectomy devices collect and remove the obstructive tissue from the artery. Others do not. One device which does remove excised tissue is disclosed in co-pending patent U.S. patent application Ser. No. 123,713 filed Nov. 23, 1987 for an invention entitled "System for, and Method of, Excising Obstructive Tissue from Lumen of Living Beings," and U.S. patent application Ser. No. 213,691 filed Jun. 30, 1988 for an invention entitled "Cutter for Atherectomy Device". Both of the applications are assigned to the same assignee as the present invention.

In addition to recovering excised tissue, the atherectomy system and method described in the above-referenced patent application Ser. No. 123,713 provides a telescopically sliding means within the handpiece (the drive unit) which can provide as much as 2.5 cm of telescopic advancement or retraction of the rotatable cutter during an excision of obstructive tissue. Further, this sliding means within the handpiece allows precise and tactile control of the cutting process through selective variation of the length of catheter, and consequently, the location of the cutter within the artery. This may, perhaps, be best understood by using the site of entry into an artery as a reference point. The obstructive tissue of interest in an arterial tree will lie at some arbitrary but fixed distance from this entry site. Hence, some arbitrary length of catheter will be required to reach any given lesion in the body. The length of the catheter, from the entry site to the obstruction, is manually fed into the artery over a guide wire using fluoroscopy for control. The proximal end of the catheter and cutter assembly is then mechanically coupled to the handpiece (i.e. drive unit) and the handpiece is further coupled to the entry site. When these cited system components have been coupled, the total length of the system, both within and without the artery, from the obstruction to the handpiece has been defined. In order to remove the obstruction, an additional length of catheter which is equal to the lesion length must still be advanced into the artery. Normally, in treating short focal lesions (obstructions), this additional length is available by extending the telescopic sliding means from within the handpiece. Unfortunately, diffuse obstructions can exceed 2.5 cm in length. Thus, some device is needed which will permit even further advancement of the catheter and cutter into the obstruction.

Accordingly, an object of the present invention is to provide a probe for controlling the cutter of an atherectomy device as it cuts a passageway through obstructive tissue in an artery. Another object of the present invention is to provide a probe for an atherectomy device which facilitates the incremental advancement of a rotating cutter and its associated torque tube beyond the support sheath within a determined safety range while moving only the portion of the sheath outside the body. Yet another object of the present invention is to provide a probe for an atherectomy device which is easily manufactured, easy to operate, and relatively inexpensive.

SUMMARY OF THE INVENTION

A preferred embodiment of an atherectomy advancing probe of the present invention comprises a distal support and a proximal support for slideably supporting a torque tube having a cutter attached at its distal end. The torque tube is rotated about its longitudinal axis by a motor which is slideably mounted inside the housing of a drive unit that is fixedly attached to the proximal support. A rod, having one end fixedly attached to the distal support is extended substantially parallel to the torque tube for selective engagement of its proximal end portion with the housing of the drive unit. Aligned adjacent and substantially parallel to the rod is an elongated advancement tape having juxtaposed dual layers which are attached between the distal support and the proximal support to surroundingly engage the torque tube. A tape divider is positioned on the advancement tape intermediate the distal support and the proximal support and a tape advancer is engageable with the tape divider to separate the layers of the advancement tape. Specifically, to separate the layers, two pins extending from the tape advancer are inserted between the layers of the tape for laterally separating the layers to advance the proximal support and the distal support toward each other. Because the housing is fixedly attached to the proximal support, this interaction causes the housing of the drive unit to advance toward the distal support.

In the operation of the atherectomy advancing probe, a guide wire is inserted into an artery and extended to and through the reduced lumen of the obstructive tissue which is to be removed. The atherectomy cutter and its associated torque tube, in combination with the tube-shaped sheath which surrounds the torque tube and is connected to the distal support of the atherectomy probe, are then introduced into the artery over the guide wire. The cutter at the distal end of the torque tube is positioned slightly beyond the distal end of the sheath and is rotated by the torque tube and advanced to cut through the obstructive tissue until further advancement is prevented by the proximal end of the torque tube abutting the proximal end of the sheath. To continue cutting through the obstructive tissue, the motor and its connected torque tube are securely engaged to the rod to hold the motor and torque tube in a fixed relationship with respect to the distal support. The tape advancer is then engaged with the tape to partially separate the layers to advance the housing of the drive unit and the proximal support toward the distal support. The motor and torque tube are then released from the rod to allow them to move longitudinally in relation to the housing of the drive unit and the distal support for incrementally cutting through the obstructive tissue. This procedure is repeated until an effective passageway has been established through the obstructive tissue.

A suction system can be engaged to the atherectomy probe for withdrawing obstructive tissue cuttings from the artery during an atherectomy procedure. Also, a port can be provided for injecting medicinal fluids into the artery during the operation.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 2 is a perspective view of the atherectomy advancing probe of FIG. 1 having an advancement tape for advancing a torque tube;

FIGS. 8A, 8B, 8C, and 8D are schematic cross-sectional views of the torque tube having a cutter and an associated support sheath illustrating the incremental advancement of the cutter as it drills through obstructive tissue in an artery in the operation of the atherectomy advancing probe of the present invention.

DESCRIPTION OF THE PREFERRED EMBODIMENT

Figure 1:
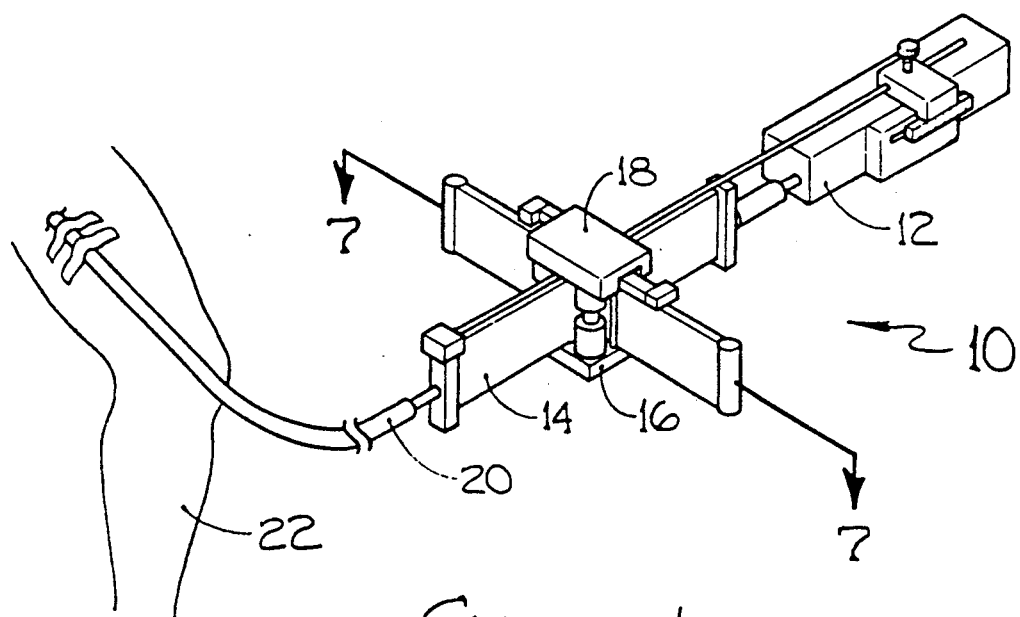
FIG. 1 is a perspective view of the preferred embodiment of an atherectomy advancing probe with a tape divider of the present invention shown in combination with a support sheath inserted into a patient.

Referring initially to FIG. 1, the present invention is shown in its intended environment. In FIG. 1, an atherectomy advancing probe, generally designated 10 is shown connected to a substantially tubular support sheath 20 which is inserted into an artery of a patient 22. The atherectomy probe 10 generally comprises a drive unit 12 operatively connected to an advancement tape 14 which is set in a tape divider 16. Tape advancer 18 is insertably mounted on tape divider 16 to incrementally advance the torque tube (not shown) for cutting obstructive tissue from the lumen of the artery.

The arrangement and cooperation of the components of atherectomy advancing probe 10 can be best seen by referencing FIG. 2. Specifically, atherectomy advancing probe 10 incrementally advances a rotating cutter 28 attached to a torque tube 30. Torque tube 30 is slideably engageable with sheath 20 and a Luer fitting 21. Luer fitting 21 is connected to a distal support 24. The distal support 24 and a proximal support 26 are interconnected by advancement tape 14. The torque tube 30 is longitudinally slideable in relation to the proximal support 26 and the distal support 24. As will be appreciated after further disclosure, tape 14 comprises two layers 13 and 15 of fastening tape for holding the torque tube 30 therebetween.

Still referring to FIG. 2, the torque tube 30 is rotated by a motor 33 (not shown In FIG. 2) which is slideably mounted inside a housing 32 of drive unit 12. An advancement lever 36, which is connected to the motor 33, is slidingly engaged with slot 34 of housing 32. A rod guide 38 is integrally connected to advancement lever 36. Rod guide 38 has a hole 39 formed therethrough and a connector 40 is threadably attached to rod guide 38 for advancement into hole 39. Housing 32 of drive unit 12 has an opening 42 to allow a rotating seal 44 to extend from the interior of drive unit 12. Connected to rotating seal 44 is a torque tube housing 46 which provides the necessary interconnection between torque tube 30 and the motor in housing 32. Torque tube housing 46 is fixedly connected to the proximal support 26 such that any longitudinal movement of proximal support 26 causes torque tube housing 46, rotating seal 44, and housing 32 of drive unit 12 to correspondingly advance in the same longitudinal direction.

A distal fitting 48 is connected to distal support 24 for fixedly holding one end of a rod 50 thereto. From its attachment to fitting 48 and support 24, rod 50 extends substantially parallel to torque tube 30 and is slideably received within hole 39 of rod guide 38. When connector 40 is threadably advanced into hole 39 of rod guide 38, rod 50 is fixedly held inside hole 39. By thus engaging rod 50 with connector 40, advancement lever 36 and motor 33 are also fixedly held in their relationship with rod 50. On the other hand, when connector 40 is disengaged from rod 50, advancement lever 36 can slide along slot 34 and, together with motor 33, move in housing 32 to correspondingly advance torque tube 30 through sheath 20.

In FIG. 2, it can be seen that tape divider 16 comprises a top plate 52 and a base plate 54 for holding a plurality of rollers 56 therebetween. Top plate 52 is positioned substantially parallel to base plate 54. Rollers 56 are cylindrical-shaped and positioned with their longitudinal axes substantially perpendicular to base plate 54 and top plate 52. Top plate 52 has a groove 53 formed therein for slideably receiving the rod 50. Tape guides 58a and 58b are held between top plate 52 and base plate 54 for guiding tape 14. Also held between top plate 52 and base plate 54 are aligning pins 60a and 60b for properly aligning tape 14. For receiving tape advancer 18, tape divider 16 has prong guides 62a and 62b formed within two rollers 56 for insertably receiving the tape advancer 18 when mounted thereon.

Figure 3:
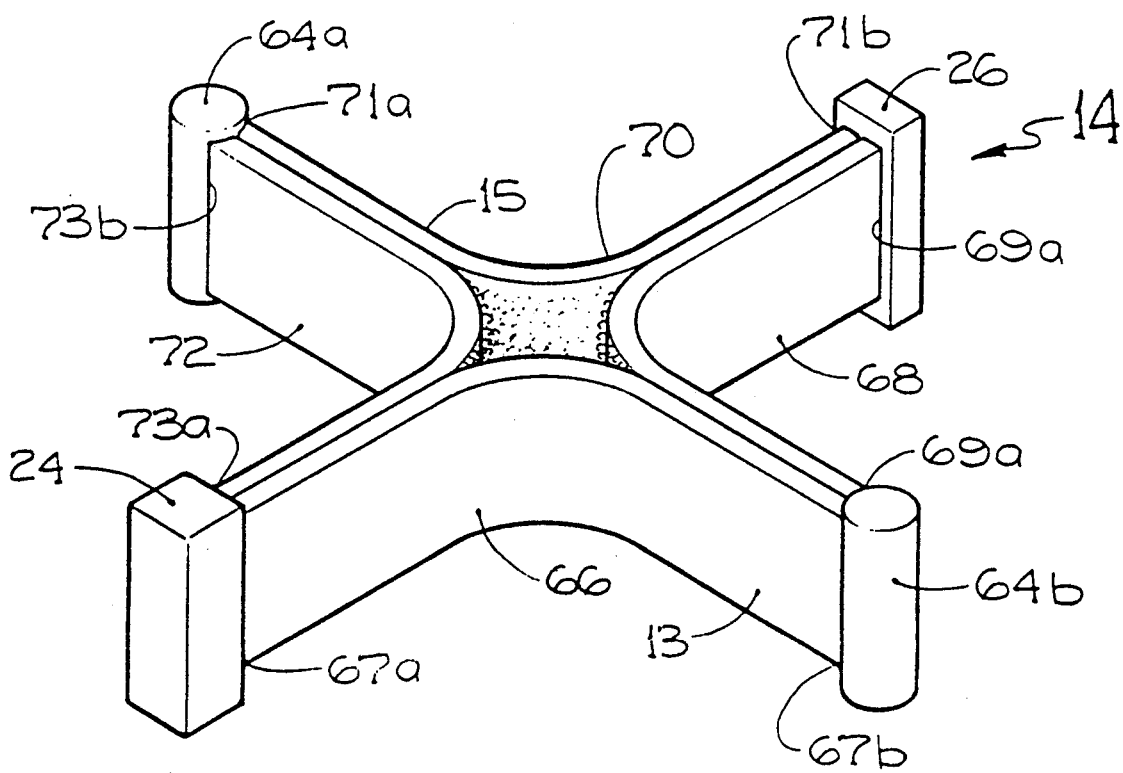
FIG. 3 is a perspective view of the advancement tape used with the atherectomy advancing probe of FIG. 2.

Referring now to FIG. 3, it can be seen that tape 14 comprises four (4) elongated strips of tape which are fixedly connected at their ends substantially as shown. As previously mentioned, tape 14 is a fastening tape, which has opposed surfaces for adhering the juxtaposed dual layers 13 and 15 together. Specifically, the fastening tape 14 includes receiving surfaces and attaching surfaces which respectively include a plurality of resilient loops and a plurality of resilient hooks for connecting layers 13 and 15 of tape 14 together.

As shown in both FIG. 2 and FIG. 3, tape 14 generally comprises a pair of juxtaposed layers 13 and 15 which are attached between distal support 24 and proximal support 26. More particularly, layer 13 of tape 14 comprises a first strip 66 with a receiving surface having a first end 67a and a second end 67b. First end 67a is connected to distal support 24 and second end 67b is connected to juncture 64b. Layer 13 also includes a second strip 68 with an attaching surface and having a first end 69a also connected to juncture 64b and a second end 69b connected to proximal support 26. Thus, first strip 66 and second strip 68, as interconnected by juncture 64b, comprise first layer 13. Still referring to FIG. 3, it will be seen that layer 15 of tape 14 comprises a third strip 70 having a receiving surface and having a first end 71a and a second end 71b connected to a first juncture 64a and proximal support 26, respectively. Further, layer 15 includes a fourth strip 72 with an attaching surface and having a first end 73a and a second end 73b. First end 73a is connected to distal support 24 and second end 73b is connected to first juncture 64a. Thus, third strip 70 and fourth strip 72 comprise second layer 15 of tape 14.

Figure 4:
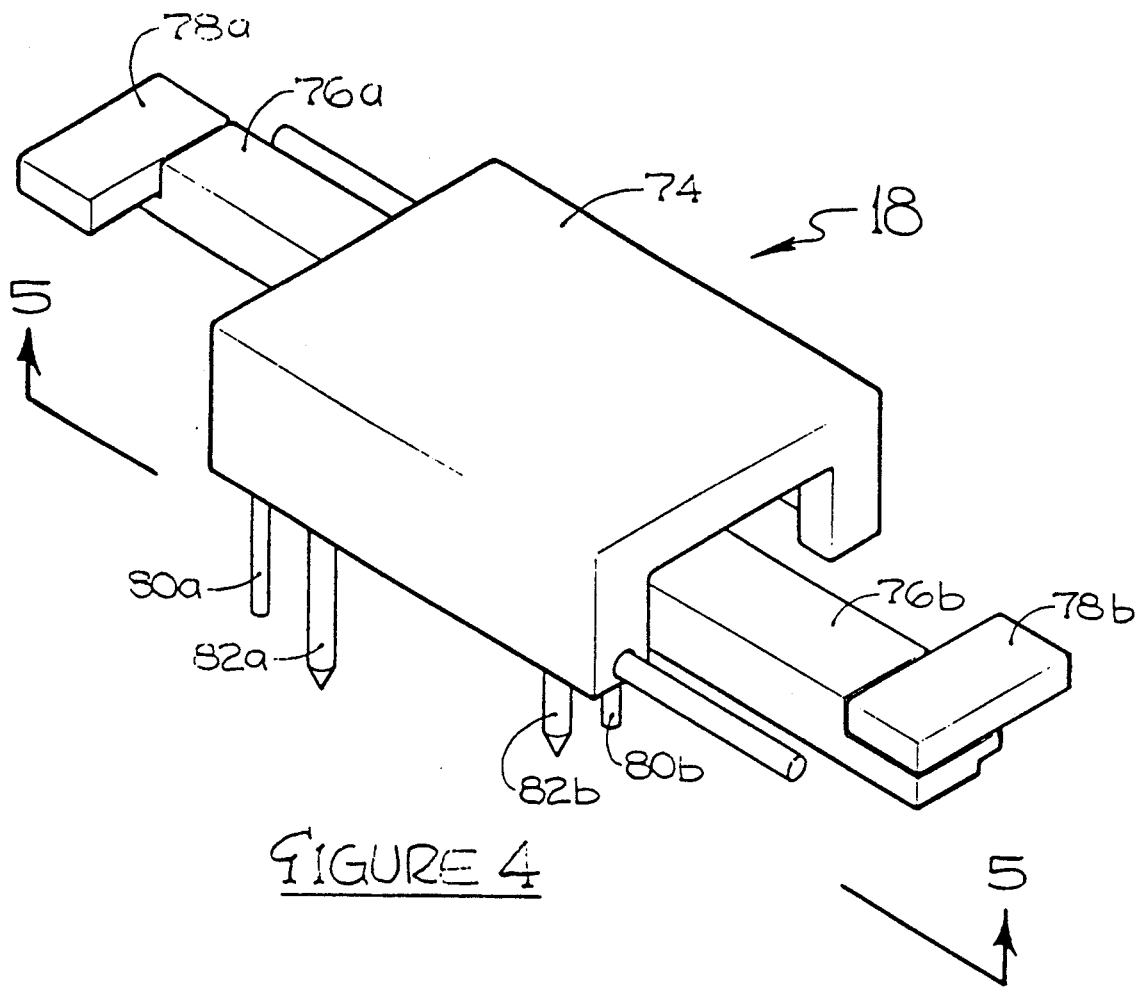
FIG. 4 is a top perspective view of the tape advancer used with the atherectomy advancing probe of FIG. 1.

Referring now to FIG. 4, it can be seen that the tape advancer 18 comprises a housing 74 for slideably supporting slides 76a and 76b therein. Finger pieces 78a and 78b are integrally connected to slides 76a and 76b and two (2) separating pins 80a and 80b extend from the tape advancer 18. Also extending from tape advancer 18 and substantially parallel to pins 80a and 80b are prongs 82a and 82b which can be slideably inserted into prong guides 62a and 62b of tape divider 16 for a purpose to be subsequently disclosed.

Figure 5:
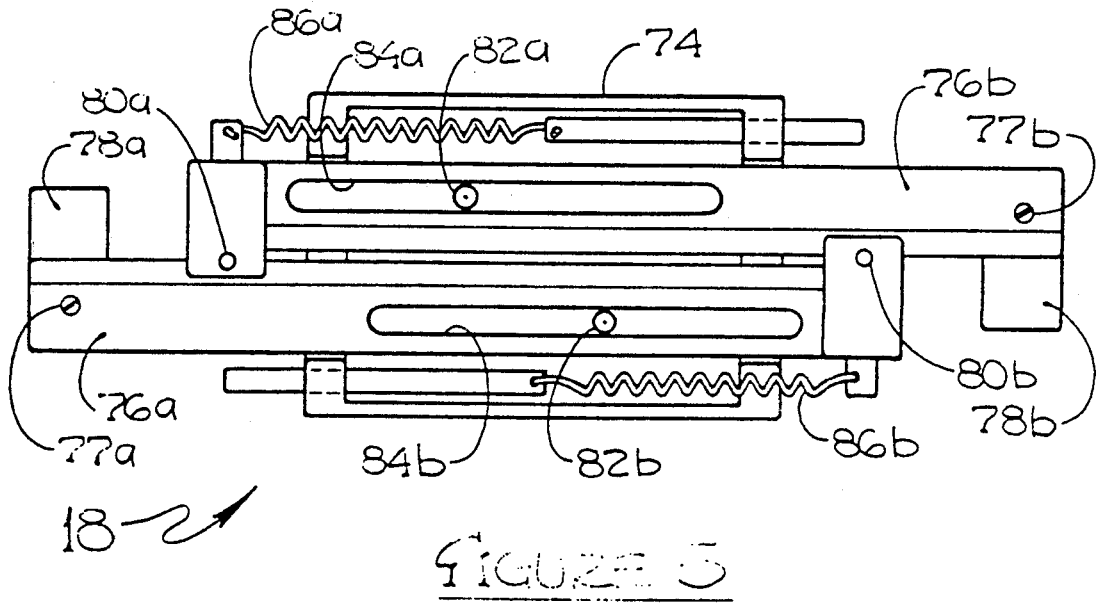
FIG. 5 is a bottom view of the tape advancer as seen along line 5—5 of FIG. 4.

Referring now to FIG. 5, a bottom view of tape advancer 18 shows that slide 76a has a slot 84b formed therein for slideably receiving prong 82b. Likewise, slide 76b has a slot 84a for slideably receiving prong 82a. Slide 76b has a spring 86a interconnecting slide 76b and housing 74 for urging the slide outward to a biased position. Similarly, slide 76a has a spring 86b interconnecting slide 76a and housing 74 for urging the slide outward to a biased position. Finally, it can be seen that finger pieces 78a and 78b are interconnected to their corresponding slides 76a and 76b by screws 77a and 77b, respectively.

OPERATION

In its operation, atherectomy advancing probe 10 requires that sheath 20, torque tube 30 and cutter 28 be inserted over a previously placed guide wire 94 and through an artery until cutter 28 of torque tube 30 abuts the obstructive tissue in the lumen of the artery. Upon rotation of torque tube 30 and advancement of lever 36, cutter 28 drills a passageway through obstructive tissue. The present invention recognizes that subsequent incremental advancement of the torque tube 30 through sheath 20 can be achieved by first separately advancing the housing 32 of exterior driving unit 12 by use of tape advancer 18.

Figure 6:
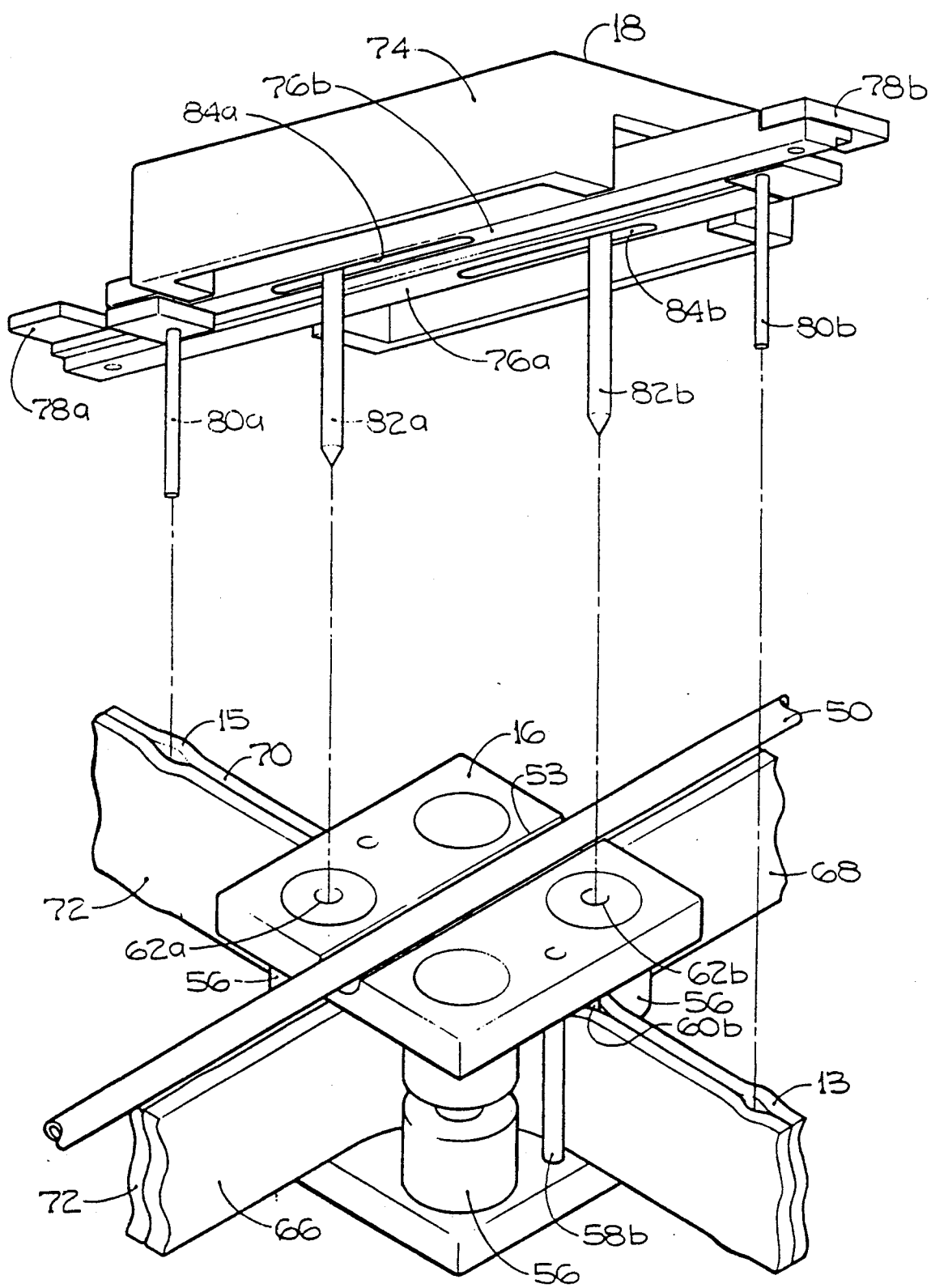
FIG. 6 is a perspective view illustrating the interconnection of the tape advancer of FIG. 5 and the atherectomy advancing probe which comprises a tape divider.

Referring now to FIG. 6, it will be seen that tape advancer 18 can be insertably mounted on tape divider 16 by slideably inserting prongs 82a and 82b into prong guides 62a and 62b of tape divider 16. With this alignment, pins 80a and 80b are respectively engaged with layers 15 and 13 of tape 14. Specifically, pin 80a is slideably interposed between third strip 70 and fourth strip 72 of layer 15. Similarly, pin 80b is slideably interposed between first strip 66 and second strip 68 of layer 13. As finger pieces 78a and 78b are slideably pushed toward one another, pins 80a and 80b correspondingly move away from one another. This interaction causes tape junctures 64a and 64b to separate and proximal support 26 to move toward distal support 24. This operation will be more easily understood with reference to FIG. 7.

Figure 7:
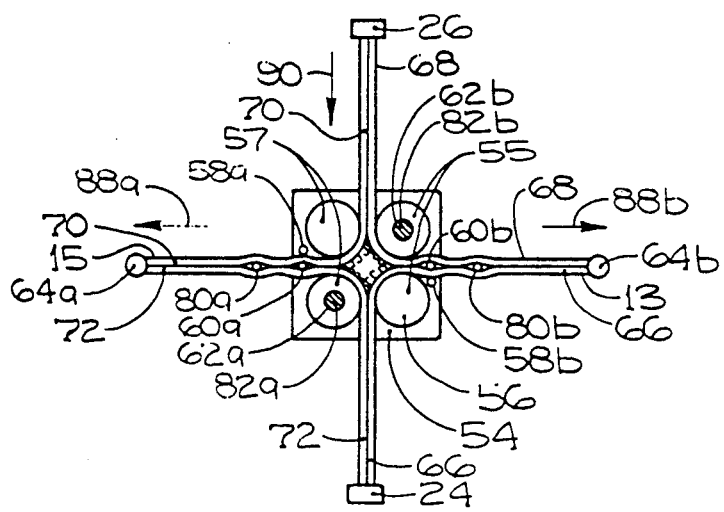
FIG. 7 is a cross-sectional view of the tape divider and the tape advancer as seen along line 7—7 of FIG. 1.

In FIG. 7, after pin 80a and pin 80b are slideably interposed between the layers 13 and 15 of tape 14 (i.e. the tape advancer 18 is engaged with tape 14 as describe above) the pins 80a and 80b are held in position with respect to layers 13 and 15 of tape 14. Movement of the pins in the direction of arrows 88a and 88b, moves the tape junctures 64a and 64b apart. Using distal support 24 as a fixed reference, this pulls proximal support 26 in the direction of arrow 90. As the junctures 64a and 64b are laterally extended, cooperating layers 13 and 15 are pressed together by operatively engaging rollers 56. Specifically, rollers 56 include a first pair of rollers 55 and a second pair of rollers 57. First strip 66 and second strip 68 are threaded between the first pair of rollers 55. Third strip 70 and fourth strip 72 are threaded between the second pair of rollers 57. Additionally, tape guides 58a and 58b provide the auxilliary guiding of the strips. Also, aligning pins 60a and 60b further align strips of tape 14 so that they will adhere to one another.

Figure 8A:
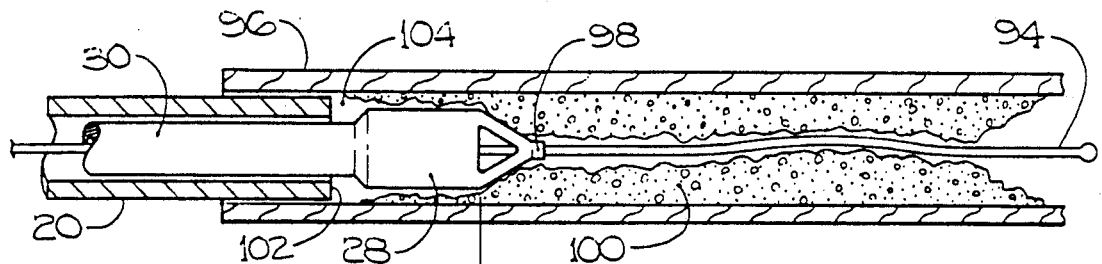
Figure 8B:
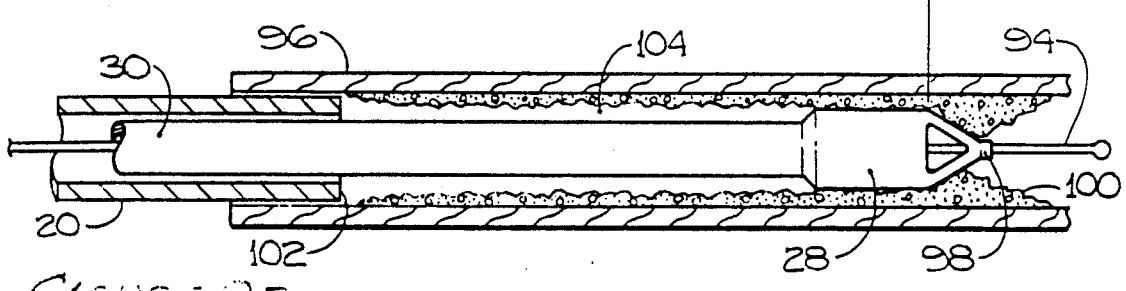

Referring now to FIGS. 8A and 8B, during an atherectomy procedure which is undertaken for the removal of obstructive tissue from an artery 96, a guide wire 94 is initially positioned inside artery 96 and extended through obstructive tissue 100. With the help of guide wire 94, torque tube 30 and surrounding sheath 20 are then inserted into artery 96 until sheath 20 is positioned within artery 96 adjacent to the obstructive tissue 100.

As seen in FIG. 8A, cutter 28 which is attached to the distal end of torque tube 30 initially extends only a short distance from the distal end of sheath 20. Cutter 28 has razor sharp blades for cutting through obstructive tissue 100 when rotated. Cutter 28 also has a hollow tip 98 through which guide wire 94 passes. Significantly, guide wire 94 helps prevent cutter 28 from deviating excessively from its intended path during operation in addition to positioning sheath 20, torque tube 30 and cutter 28 within artery 96. This limitation helps to reduce the possibility that cutter 28 will penetrate artery 96. As illustrated in FIGS. 8A and 8B, when torque tube 30 and cutter 28 are rotated and advanced by a surgeon, a passageway 104 is drilled through obstructive tissue 100 in artery 96.

Referring back to FIG. 2, it can be seen that the advancement of cutter 28 is eventually stopped when lever 36 has moved to the most forward (i.e. distal) position in slot 34 of housing 32. As can be appreciated, this interaction halts the advancement of cutter 28 and stops further cutting of the passageway 104 through the obstructive tissue 100. In order to continue drilling through the obstructive tissue 100, it is necessary to reposition the lever 36 at the rearmost (i.e. proximal) position in slot 34.

Figure 9A:
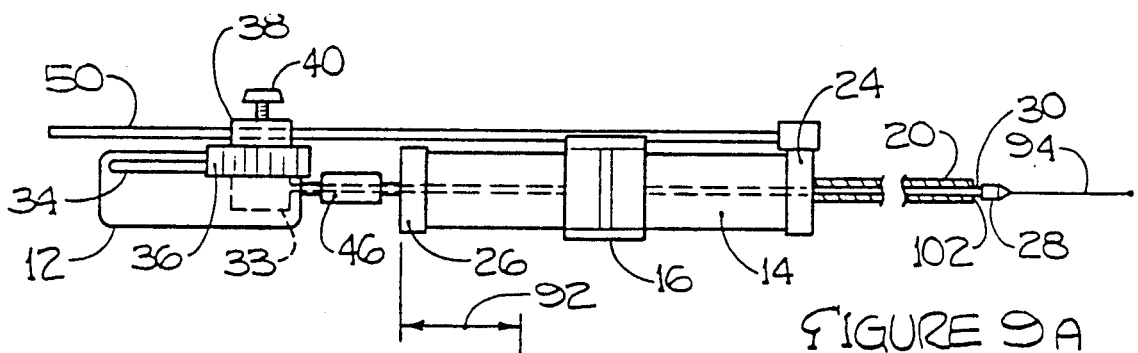
FIGS. 9A, 9B and 9C are schematic side views of the atherectomy advancing probe of FIG. 1 illustrating operation of the probe as it incrementally advances the torque tube and the cutter.
Figure 9B:
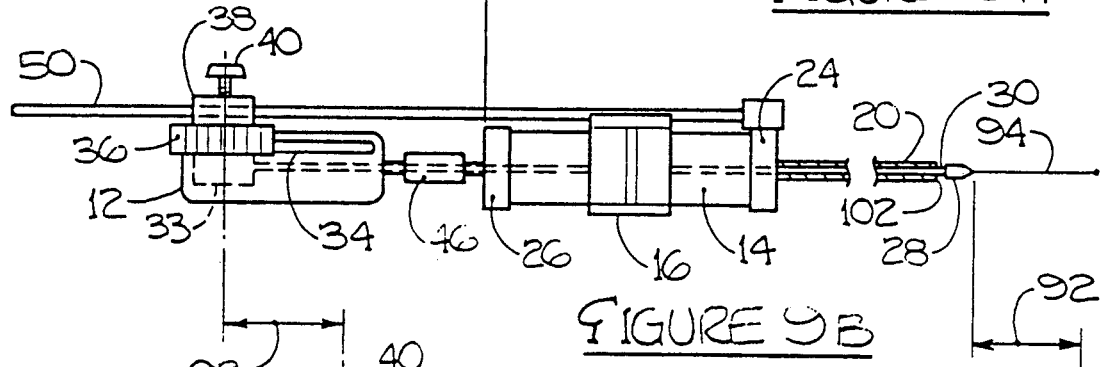
Figure 9C:
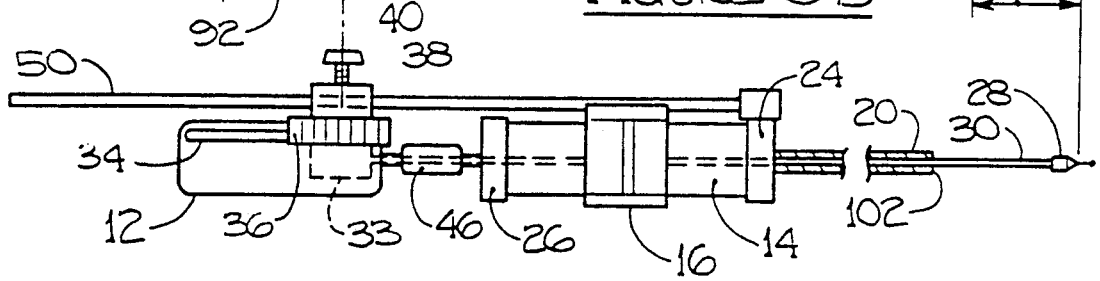

Referring now to FIGS. 9A, 9B, and 9C, it is to be appreciated at the outset that distal support 24 is held stationary during the operation. Consequently, sheath 20 is also held stationary. With this in mind, these figures illustrate what can be done when lever 36 can no longer be used to advance torque tube 30 and cutter 28 through obstructive tissue 100. Referring specifically to FIG. 9A, threaded connector 40 is selectively engaged with rod guide 38 to fixedly hold advancement lever 36 and motor 33 in their relationship with rod 50. When tape advancer 18 is connected to tape divider 16 and manipulated to advance proximal support 26 toward distal support 24, the drive unit 12 and housing 32 also move in a distal direction toward support 24. As can be seen in FIG. 9B, for each incremental advancement, proximal support 26, drive unit 12 and housing 32 are advanced by a distance generally designated 92. Even though drive unit 12 has advanced a distance 92, advancement lever 36, motor 33 and torque tube 30 have been fixedly held in place relative to distal support 24 by their interaction with rod 50. In FIG. 9B, when proximal support 26 is advanced toward distal support 24, cutter 28 and sheath 20 are not advanced in a distal direction.

Cross-referencing FIGS. 8B and 9C, it will be seen that when threaded connector 40 is disengaged from rod guide 38, advancement lever 36 and attached motor 33 can be manually advanced in the distal direction. This advancement of the advancement lever 36 moves the torque tube 30 in a distal direction and correspondingly advances the cutter 28 by an incremental distance 92. Referring to FIG. 8B, it can be appreciated that passageway 104 is also extended by a distance 92.

Following the above procedure, passageway 104 may be extended further through the obstructive tissue 100 by sequentially and alternatingly advancing proximal support 26 and advancement lever 36 toward distal support 24. In order to have a complete passageway 104 through obstructive tissue 100 the above-described procedure is repeated until a continuous passageway is formed through the obstructive tissue 100. The extent to which cutter 28 can be advanced beyond the distal end of sheath 20 will be limited by the length to which tape 14 can be longitudinally shortened. This limitation can be used to advantage in that deviations of cutter 28 from its intended path can be precisely controlled by limiting the unsupported exposure of cutter 28.

In the preferred embodiment, each incremental advancement as illustrated above is approximately two and one-half (2.5) cm. Generally, the total travel distance of advancement will be approximately twenty-five (25) cm in the preferred embodiment, which corresponds to approximately ten (10) incremental advancements by atherectomy advancing probe 10. It should be understood that the preferred embodiment can be operated by one person during surgery.

A suction system can be engaged to the atherectomy probe 10 for withdrawing obstructive tissue cuttings from artery 96 during the atherectomy procedure. Removing the obstructive tissue 100 from the artery 96 reduces the potential for a recurrence of the blocked artery 96. Also, a port can be provided in the atherectomy probe 10 for injecting needed medicinal fluids therethrough. Such fluids then enter the patient's blood stream through the torque tube 30.

While the particular atherectomy advancing probe as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An atherectomy probe for incrementally advancing a rotatable cutter to remove obstructive tissue from an artery comprising:
   a distal support;
   a proximal support;
   a torque tube slidably held by said distal support and said proximal support, said torque tube having a distal end operatively engageable with the cutter;
   a motor operatively connected to the proximal end of said torque tube for rotating said torque tube;
   a connector for selectively holding said motor stationary with respect to said distal support;
   means for selectively advancing said proximal support toward said distal support while said connector holds said motor stationary; and
   means for incrementally moving said motor toward said distal support to the extent allowed by said proximal support to advance the cutter from said distal support when said connector is released.

2. An atherectomy probe as recited in claim 1 further comprising a sheath surrounding said torque tube, said sheath being attached to said distal support and extending distally therefrom.

3. An atherectomy probe as recited in claim 2 wherein said connector further comprises a rod extending substantially parallel to said torque tube, said rod being selectively engageable with said motor and fixedly attached to said distal support.

4. An atherectomy probe as recited in claim 3 further comprising:
   a housing for holding said motor, said motor being coupled to said torque tub end longitudinally slidable in said housing along an axis substantially parallel to said rod, said housing including a rod guide attached thereto in surrounding relationship to said rod, said connector being operatively engaged with said rod guide for fixedly holding said motor relative to said distal support.

5. An atherectomy probe as recited in claim 4 further comprising a torque tube housing for interconnecting said torque tube to said motor.

6. An atherectomy probe as recited in claim 5 further comprising an advancement tape having juxtaposed dual layers attached between said distal support and said proximal support, said advancement tape having fastening surfaces for adhering said juxtaposed dual layers of said advancement tape together, said fastening surfaces comprising a receiving surface on one of said layers and an attaching surface on the other of said layers for selective attachment.

7. An atherectomy probe as recited in claim 6 wherein said receiving surface includes a plurality of resilient loops and said attaching surface includes a plurality of resilient hooks.

8. An atherectomy probe as recited in claim 6 wherein said dual layers of said tape comprise:
   a first juncture on one of said dual layers;
   a second juncture on the other of said dual layers;
   a first strip having a receiving surface with a first end connected to said distal support and a second end connected to said first juncture;
   a second strip having an attaching surface with a first end connected to said first juncture and a second end connected to said proximal support, said first strip and said second strip combine to form said first layer;
   a third strip having a receiving surface with a first end connected to said second juncture and a second end connected to said proximal support; and
   a fourth strip having an attaching surface with a first end connected to said distal support and second end connected to said second juncture, said third strip and said fourth strip combine to form said second layer.

9. An atherectomy probe as recited in claim 8 further comprising a tape divider operatively engageable with said tape, said tape divider comprising:
   a base plate;
   a top plate positioned substantially parallel to said base plate, said top plate having a groove formed therein for slideably receiving said rod;
   four rollers held between said top plate and said base plate for meshing said strips of said layer together to form a lateral extension, said rollers being cylindrical-shaped and positioned substantially perpendicular with said plates to form a two-by-two matrix;
   two tape guides held between said top plate and said base plate for guiding said dual layers when laterally extended;
   two aligning pins held between said top plate and said base plate and positioned between said dual layers of said tape for aligning said dual layers when laterally extended; and
   two prong guides formed within two of said rollers being diagonally separated.

10. An atherectomy probe as recited in claim 9 wherein said advancing means comprises a tape advancer mountable on said top plate of said tape divider with tape disposed therein, said tape advancer having:
   a tape advancer housing;
   two parallel slides slideably restrained within said housing for simultaneous movement in directions opposite one another;
   two finger pieces integrally connected to said slides;
   two mounting prongs fixed to said housing perpendicular thereto for slideably inserting into said prong guides of said tape divider;
   a pin fixed to each of said slides and extending substantially parallel to said prongs; and
   a spring interconnected between each said slide and said housing for resisting the movement of said slides.

11. An atherectomy probe as recited in claim 10 wherein said pins are insertably engaged between said strips and slideably separated by engaging said tape divider to distance said first and said second juncture and form said lateral extensions, said pins of said slides are returned to a disengaged position by said resisting springs.

12. An atherectomy probe for incrementally advancing a rotatable cutter to remove obstructive tissue from an artery, the probe comprising:
   a distal support;
   a proximal support;
   a torque tube having a distal end connectable to the cutter, said torque tube longitudinally slidable in relation to said proximal support and said distal support;
   a drive unit operatively coupled to said proximal support, said drive unit having a motor slidably mounted in a drive unit housing, said motor being operatively coupled to the proximal end of said torque tube for rotating said torque tube about a longitudinal axis;
   a rod fixedly attached to said distal support and extending substantially parallel to said torque tube, said rod being selectively engageable with said motor for securing said torque tube from longitudinally sliding with respect to said distal support;
   an elongated advancement tape having juxtaposed dual layers attached between said distal support and said proximal support, said advancement tape having said torque tube interposed between said layers;
   a tape divider operatively engageable with said advancement tape for aligning said tape;
   a tape advancer for cooperating with said tape divider, said tape advancer having two pins which insert between said layers for laterally extending each said layer to advance said proximal support toward said distal support; and
   an advancement lever connected to said motor for incrementally advancing said torque tube longitudinally in a distal direction in relation to said distal support.

13. An atherectomy probe as recited in claim 12 wherein said drive unit comprises:
   a rod guide having an opening for slideably receiving said rod and being integrally connected to said advancement lever; and
   a connector operatively engageable with said rod guide for fixedly holding said rod inside said opening of said rod guide.

14. An atherectomy probe as recited in claim 13 wherein said advancement tape comprises fastening surfaces for adhering said juxtaposed dual layers together, said advancement tape having a receiving surface and an attaching surface for selective attachment.

15. An atherectomy probe as recited in claim 14 wherein said receiving surface includes a plurality of resilient loops and said attaching surface includes a plurality of resilient hooks.

16. An atherectomy probe as recited in claim 15 wherein said dual layers of said tape comprise:
   a first juncture on one of said dual layers;

a second juncture on the other of said dual layers;

a first strip having a receiving surface with a first end connected to said distal support and a second end connected to said first juncture;

a second strip having an attaching surface with a first end connected to said first juncture and a second end connected to said proximal support, said first strip and said second strip combine to form said first layer;

a third strip having a receiving surface with a first end connected to said second juncture and a second end connected to said proximal support; and a fourth strip having an attaching surface with a first end connected to said distal support and second end connected to said second juncture, said third strip and said fourth strip combine to form said second layer.

17. An atherectomy probe as recited in claim 16 wherein said tape divider comprises:

a base plate;

a top plate positioned substantially parallel to said base plate, said top plate having a groove formed therein for slideably receiving said rod;

four rollers held between said top plate and said base plate for meshing said strips of said layers together to form a lateral extension, said rollers being cylindrical-shaped and positioned substantially perpendicular with said plates to form a two-by-two matrix;

two tape guides held between said top plate and said base plate for guiding said layers when laterally extended;

two aligning pins held between said top plate and said base plate and positioned between said layers for aligning said layers when laterally extended; and two prong guides formed within two of said rollers being diagonally separated.

18. An atherectomy probe as recited in claim 17 wherein said advancing means comprises a tape advancer mountable on said top plate of said tape divider with tape disposed therein, said tape advancer comprising:

a tape advancer housing;

two parallel slides slideably restrained inside said housing for simultaneous movement in directions opposite one another;

two finger pieces integrally connected to said slides;

two mounting prongs fixed to said housing perpendicular thereto for slideably inserting into said prong guides of said tape divider;

a pin fixed to each of said slides and extending substantially parallel to said prongs for slideable engagement between said layers; and a spring interconnected between each said slide and said housing for resisting the movement of said slides.

19. An atherectomy probe as recited in claim 18 wherein said pins are insertably engaged between said strips and slideably separated by engaging said tape divider to distance said first and said second juncture and form said lateral extensions, said pins of said slides are returned to a disengaged position by said resisting springs.

20. A method for incrementally advancing a torque tube with a cutter through obstructive tissue in an artery to cut a continuous passageway during an atherectomy procedure by manipulating an atherectomy probe having a distal support, a proximal support, a housing attached to the proximal support and a motor operatively connected to said torque tube for rotating said torque tube, said motor being slidably mounted in said housing and selectively attachable to said distal support, the method comprising the steps of:

(a) inserting said cutter coupled to the distal end of said torque tube through said artery until said cutter contacts said obstructive tissue;

(b) selectively securing said torque tube from longitudinally sliding with respect to said distal support;

(c) advancing said housing and said proximal support toward said distal support;

(d) releasing said torque tube to longitudinally slide with respect to said distal support; and (e) moving said torque tube longitudinally in a distal direction in relation to said distal support to incrementally cut through said obstructive tissue.

21. A method as recited in claim 20 wherein said step of inserting said cutter comprises the steps of:

(a) sliding a guide wire through said artery and pass said obstructive tissue of said artery;

(b) inserting the proximal end of said guide wire through said cutter;

(c) advancing said cutter along said guide wire to position said cutter inside said artery to contact said obstructive tissue.

* * * * *